US008888707B2

(12) United States Patent
Shirasaki et al.

(10) Patent No.: US 8,888,707 B2
(45) Date of Patent: Nov. 18, 2014

(54) BLOOD PRESSURE MEASUREMENT APPARATUS

(75) Inventors: Osamu Shirasaki, Tokyo (JP); Takashi Watanabe, Kyoto (JP); Mitsuo Kuwabara, Osaka (JP); Kazuomi Kario, Tochigi (JP)

(73) Assignees: Omron Healthcare Co., Ltd., Kyoto (JP); Jichi Medical University, Tochigi (JP)

( * ) Notice: Subject to any disclaimer, the term of this patent is extended or adjusted under 35 U.S.C. 154(b) by 0 days.

(21) Appl. No.: 14/116,822

(22) PCT Filed: May 16, 2012

(86) PCT No.: PCT/JP2012/062506
§ 371 (c)(1),
(2), (4) Date: Nov. 11, 2013

(87) PCT Pub. No.: WO2012/161049
PCT Pub. Date: Nov. 29, 2012

(65) Prior Publication Data
US 2014/0081101 A1    Mar. 20, 2014

(30) Foreign Application Priority Data

May 24, 2011   (JP) .................................. 2011-115846

(51) Int. Cl.
| A61B 5/02 | (2006.01) |
| A61B 5/0205 | (2006.01) |
| A61B 5/00 | (2006.01) |
| A61B 5/0225 | (2006.01) |
| A61B 5/1455 | (2006.01) |
| A61B 5/08 | (2006.01) |
| A61B 5/024 | (2006.01) |
| A61B 5/022 | (2006.01) |

(52) U.S. Cl.
CPC ............ *A61B 5/02255* (2013.01); *A61B 5/0205* (2013.01); *A61B 5/4818* (2013.01); *A61B 5/02416* (2013.01); *A61B 5/14551* (2013.01); *A61B 5/6826* (2013.01); *A61B 5/02241* (2013.01); *A61B 5/0826* (2013.01); *A61B 5/022* (2013.01)
USPC ........................................ 600/485; 600/490

(58) Field of Classification Search
None
See application file for complete search history.

(56) References Cited

U.S. PATENT DOCUMENTS

| 5,564,427 | A * | 10/1996 | Aso et al. ...................... 600/494 |
| 7,927,283 | B2 * | 4/2011 | Riobo Aboy .................. 600/490 |
| 8,062,227 | B2 * | 11/2011 | Cho et al. ....................... 600/508 |
| 2005/0187480 | A1* | 8/2005 | Kario et al. .................... 600/483 |
| 2008/0287814 | A1* | 11/2008 | Muehsteff et al. ............. 600/490 |
| 2011/0230729 | A1* | 9/2011 | Shirasaki et al. ............. 600/301 |

FOREIGN PATENT DOCUMENTS

| JP | 62-155829 A | 7/1987 |
| JP | 6-70889 A | 3/1994 |
| JP | 09-299339 A | 11/1997 |
| JP | 2006-102260 A | 4/2006 |
| JP | 2007-252747 A | 10/2007 |
| JP | 2009-247386 A | 10/2009 |
| WO | 2009/020114 A1 | 2/2009 |

OTHER PUBLICATIONS

International Search Report for corresponding International Application No. PCT/JP2012/062506, mailed Aug. 21, 2012 (4 pages)
International Preliminary Report on Patentability for corresponding International Application No. PCT/JP2012/062506, mailed Dec. 19, 2012 (14 pages).
O. Shirasaki et al.; "A New Technique for Detecting Sleep Apnea-Related "Midnight" Surge of Blood Pressure;" Business Development Center, Omron Healthcare, Co., Ltd., et al.; Jun. 16, 2006 (pp. 695-702) (8 pages).

* cited by examiner

*Primary Examiner* — Etsub Berhanu
(74) *Attorney, Agent, or Firm* — Osha Liang LLP

(57) ABSTRACT

A blood pressure measurement apparatus for measuring blood pressure in a predetermined period includes a blood pressure measuring unit for measuring the blood pressure of a subject, an information acquiring unit for acquiring information that is related to variation in blood pressure and changes in a time-series in the predetermined period, a determining unit for determining whether or not the information acquired by the information acquiring unit satisfies a predetermined condition, and a trigger output unit for, in a case where the determining unit determines that the predetermined condition is satisfied, causing the blood pressure measuring unit to start and execute blood pressure measurement. The predetermined condition is expressed as a function of time that varies and is measured in the predetermined period.

10 Claims, 15 Drawing Sheets

| | No. | Time | | ... | SBP | DBP | ID PL |
|---|---|---|---|---|---|---|---|
| R— | 1 | T(1) | | : | SBP(1) | DBP(1) | PL(1) |
| R— | 2 | T(2) | | : | SBP(2) | DBP(2) | PL(2) |
| | : | : | | : | : | : | : |

BLOOD PRESSURE MEASUREMENT APPARATUS

TECHNICAL FIELD

The present invention relates to a blood pressure measurement apparatus, and in particular to a blood pressure measurement apparatus that controls the start timing of blood pressure measurement.

BACKGROUND ART

Obstructive sleep apnea (OSA) is a disorder in which the respiratory tract is physically obstructed during sleep, and respiration stops for as long as two minutes. Blood pressure temporarily rises in an apnea attack (referred to hereinafter as a nocturnal blood pressure surge). For example, a blood pressure that is normally 120 to 130 mmHg rises to over 200 mmHg. Accordingly, each time an apnea attack occurs, there is the risk of sudden death, stroke, or a cardiovascular event such as heart failure. The ability to accurately measure a nocturnal blood pressure surge is therefore in demand.

When measuring a nocturnal blood pressure surge, the blood oxygen saturation level decreases when respiration stops. In view of this, Patent Literature 1 (JP S62-155829A) and Non-Patent Literature 1 (A New Technique for Detecting Sleep Apnea-Related "Midnight" Surge of Blood Pressure, Shirasaki et al., Hypertens Res Vol. 29, No. 9 (2006), p. 695-702) propose methods in which the blood oxygen saturation level is measured with an oximeter, and blood pressure measurement is started when the measured blood oxygen saturation level falls below a set reference.

CITATION LIST

Patent Literature

Patent Literature 1: JP S62-155829A

Non-Patent Literature

Non-Patent Literature 1: A New Technique for Detecting Sleep Apnea-Related "Midnight" Surge of Blood Pressure, Shirasaki et al., Hypertens Res Vol. 29, No. 9 (2006), p. 695-702

SUMMARY OF INVENTION

Technical Problem

Patients with severe OSA have several hundred apnea attacks per night, each of which is accompanied by hypoxia. Accordingly, in the case where blood pressure measurement is started when the blood oxygen saturation level falls below a manually set reference as in Patent Literature 1, blood pressure measurement is performed an very large number of times with a patient who has severe OSA, and the subject's sleep is significantly inhibited.

Also, in Non-Patent Literature 1, there is an additional function in which a threshold value is first set to a relatively high level, the lowest value of the blood oxygen saturation level that appears after the start of measurement is successively stored, and blood pressure measurement is performed when the blood oxygen saturation level falls below the previous lowest value. Doing this enables performing automatic individual adjustment of the threshold value for a range of patients, from mild sufferers to severe sufferers. However, this method has the problem that if the most severe low respiration state appears during the initial stage of sleep in one night, blood pressure measurement will not be performed at all thereafter.

An object of the present invention is to provide a blood pressure measurement apparatus that acquire a pattern of blood pressure variation over the entirety of a predetermined period.

Solution to Problem

One aspect of the present invention is a blood pressure measurement apparatus for measuring blood pressure in a predetermined period, including: a blood pressure measuring unit for measuring the blood pressure of a subject; an information acquiring unit for acquiring information that is related to variation in blood pressure and changes in a time-series in the predetermined period; a determining unit for determining whether or not the information acquired by the information acquiring unit satisfies a predetermined condition; and an execution unit for, in a case where the determining unit determines that the predetermined condition is satisfied, causing the blood pressure measuring unit to start and execute blood pressure measurement, wherein the predetermined condition is expressed as a function of time that varies and is measured in the predetermined period.

Advantageous Effects of Invention

According to the present invention, it is possible to acquire a pattern of blood pressure variation over the entirety of a predetermined period.

DESCRIPTION OF EMBODIMENTS

Embodiments of the present invention will be described in detail below with reference to the drawings. Note that like reference signs in the figures denote corresponding or the same portions, and redundant descriptions will not be given for them.

In these embodiments, information excluding the blood pressure of a subject is acquired, and a blood pressure measurement unit is started based on the acquired information. The term "start" used here refers to starting blood pressure measurement-related processing performed by the blood pressure measurement unit.

Embodiment 1

Blood Oxygen Saturation Level

In Embodiment 1, the blood oxygen saturation level of a subject is monitored, and a blood pressure measurement unit is started based on the blood oxygen saturation level in a time-series obtained as a result of the monitoring.

Hardware Configuration

Figure 1:
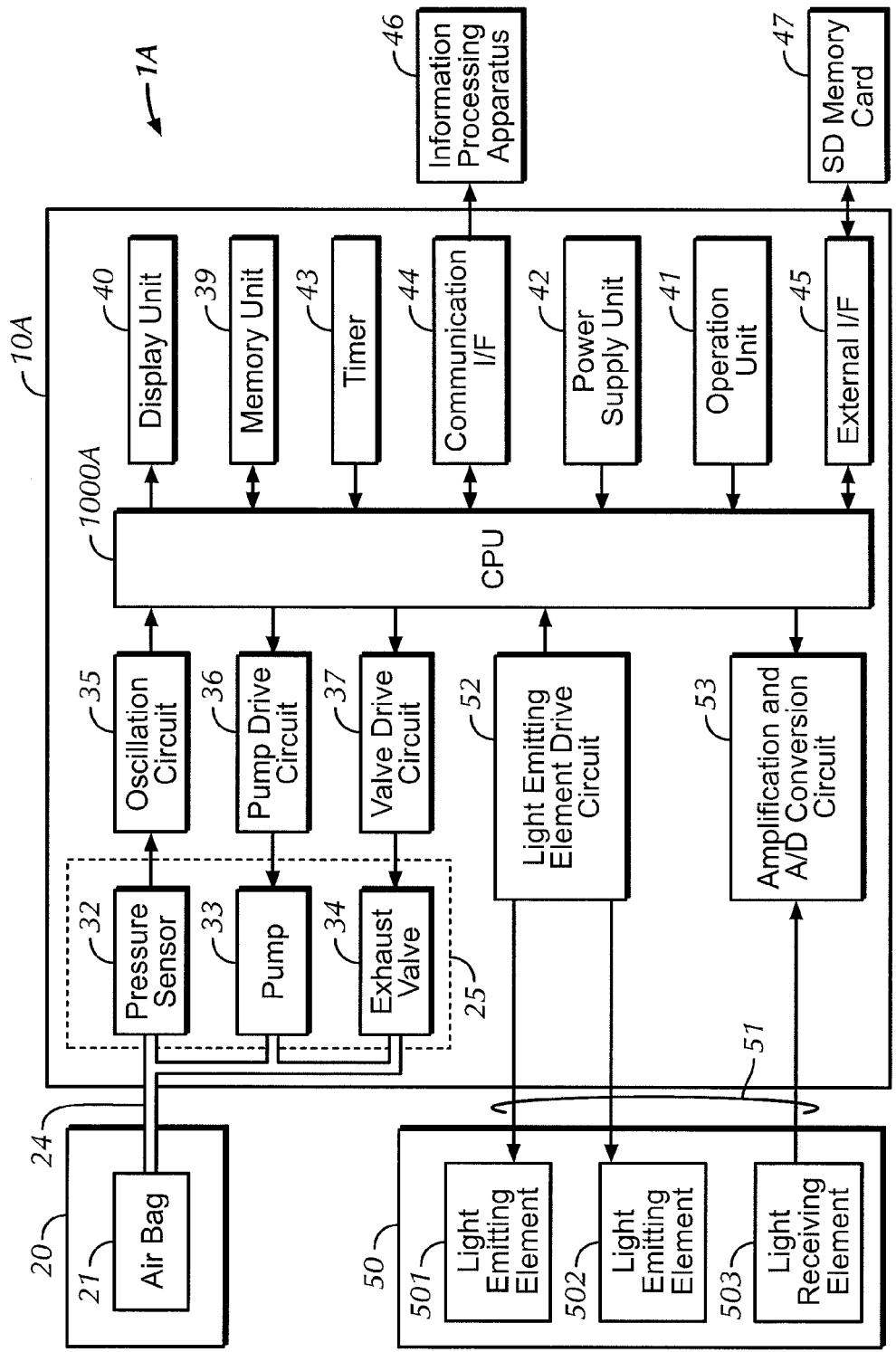
FIG. 1 shows a hardware configuration of a blood pressure measurement apparatus according to an embodiment of the present invention.

FIG. 1 shows the hardware configuration of a blood pressure measurement apparatus 1A according to an embodiment of the present invention. As shown in FIG. 1, the blood pressure measurement apparatus 1A includes a body unit 10A, a cuff 20 that is wound around a blood pressure measurement site (e.g., upper arm) on the subject, an air tube 24 for connecting the body unit 10A and the cuff 20, and a sensor unit 50 for fitting on a measurement site for measuring the blood oxygen saturation level (e.g., fingertip). The body unit 10A and the sensor unit 50 are electrically connected via wiring 51.

The body unit 10A is provided with a display unit 40 for displaying measurement results and the like, and an operation unit 41 for receiving the input of instructions from a user (typically, the subject). The operation unit 41 includes, for example, a switch operated to switch the power on/off, a switch operated to identify the subject, switches operated to input instructions to start and stop measurement, and a switch operated to input an instruction to readout and display information regarding past measured data. The display unit 40 is configured by a liquid crystal display or the like.

The cuff 20 of the blood pressure measurement apparatus 1A includes an air bag 21 that is filled with air. The air bag 21 is connected to an air system 25 built into the body unit 10A via the air tube 24.

The air system 25 includes a capacitance type pressure sensor 32 for detecting the pressure inside the air bag 21 (referred to hereinafter as the "cuff pressure"), a pump 33 for supplying air to the air bag 21, and an exhaust valve 34 that is opened and closed to allow air to flow into or out of the air bag 21.

Figure 2:
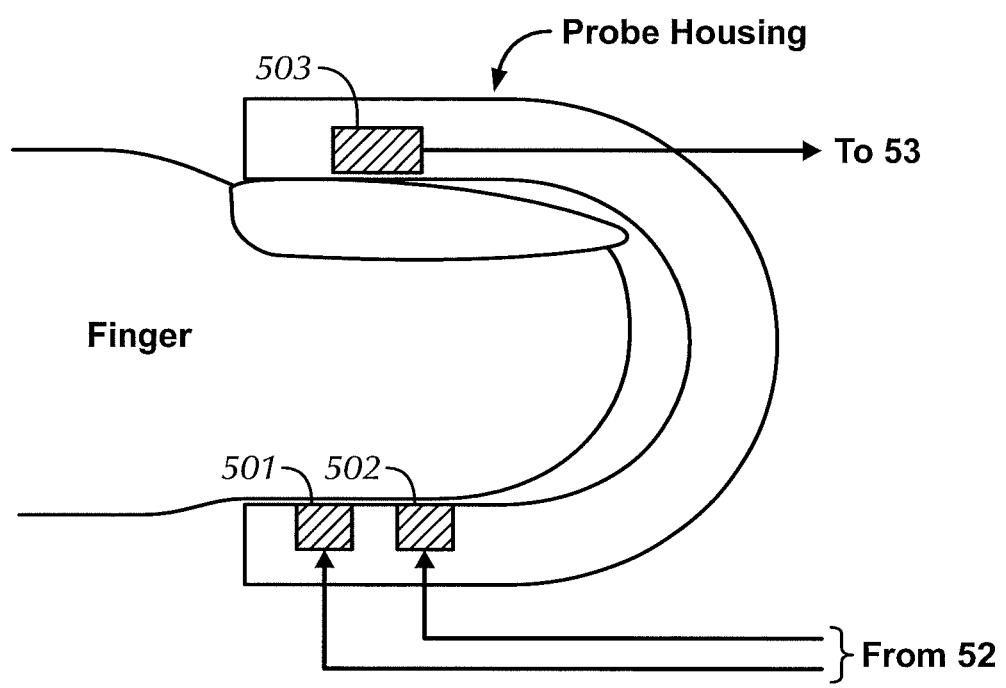
FIG. 2 is a diagram showing how a pulse oximeter according to Embodiment 1 of the present invention is fitted to a measurement site.

The sensor unit 50 corresponds to a so-called pulse oximeter. FIG. 2 shows how the pulse oximeter according to Embodiment 1 of the present invention is fitted to a measurement site. As shown in FIG. 2, the pulse oximeter includes a probe housing that is fitted to a measurement site that infrared light easily passes through, such as a fingertip. The probe housing includes at least two light emitting elements 501 and 502 that emit infrared light having different center wavelengths, and a light receiving element 503 that detects the amount of infrared light that was emitted from the light emitting elements and passed through the measurement site.

The body unit 10A includes a light emitting element drive circuit 52 that controls the light emitting operation of the light emitting elements 501 and 502, and an amplification and A/D (Analog/Digital) conversion circuit 53 that amplifies the output of the light receiving element 503 separately according to wavelength and subjects it to A/D conversion.

The body unit 10A further includes a CPU (Central Processing Unit) 1000A for performing various types of arithmetic processing, a power supply unit 42, a memory unit 39 that includes a ROM (Read Only Memory), a RAM (Random Access Memory), a non-volatile memory, or the like for storing various types of data and programs, a timer 43 for measuring and outputting the current time (year, month, day, hour, minute, second), a communication I/F (interface) 44 that controls communication with an information processing apparatus 46 and the CPU 1000A, and an external I/F 45 to and from which various types of recording media such as a SD memory card (Secure Digital memory card) 47 can be mounted and removed, and that accesses the mounted recording medium under control of the CPU 1000A. Here, there are no limitations on the information processing apparatus 46 as long as it is an apparatus that includes a communication function, a data processing function, and a function for outputting data with a display or the like.

With regard to the air system 25, the body unit 10A includes an oscillation circuit 35, a pump drive circuit 36 for driving the pump 33, and a valve drive circuit 37 for driving the exhaust valve 34.

The pump drive circuit 36 controls the driving of the pump 33 based on a control signal from the CPU 1000A. The valve drive circuit 37 controls the opening/closing of the exhaust valve 34 based on a control signal from the CPU 1000A.

The capacitance value of the pressure sensor 32 changes according to the cuff pressure, and a signal indicating the capacitance value is output after being amplified by an amplifier (amplification circuit) built into the pressure sensor 32. Based on the output signal from the pressure sensor 32, the oscillation circuit 35 outputs a signal whose oscillation frequency corresponds to the capacitance value of the pressure sensor 32 to the CPU 1000A. The CPU 1000A detects the cuff pressure by converting the signal obtained from the oscillation circuit 35 into a pressure.

The power supply unit 42 supplies power to the CPU 1000A in accordance with a power on instruction from the operation unit 41. The CPU 1000A outputs the supplied power to various units.

Functional Configuration

Figure 3:
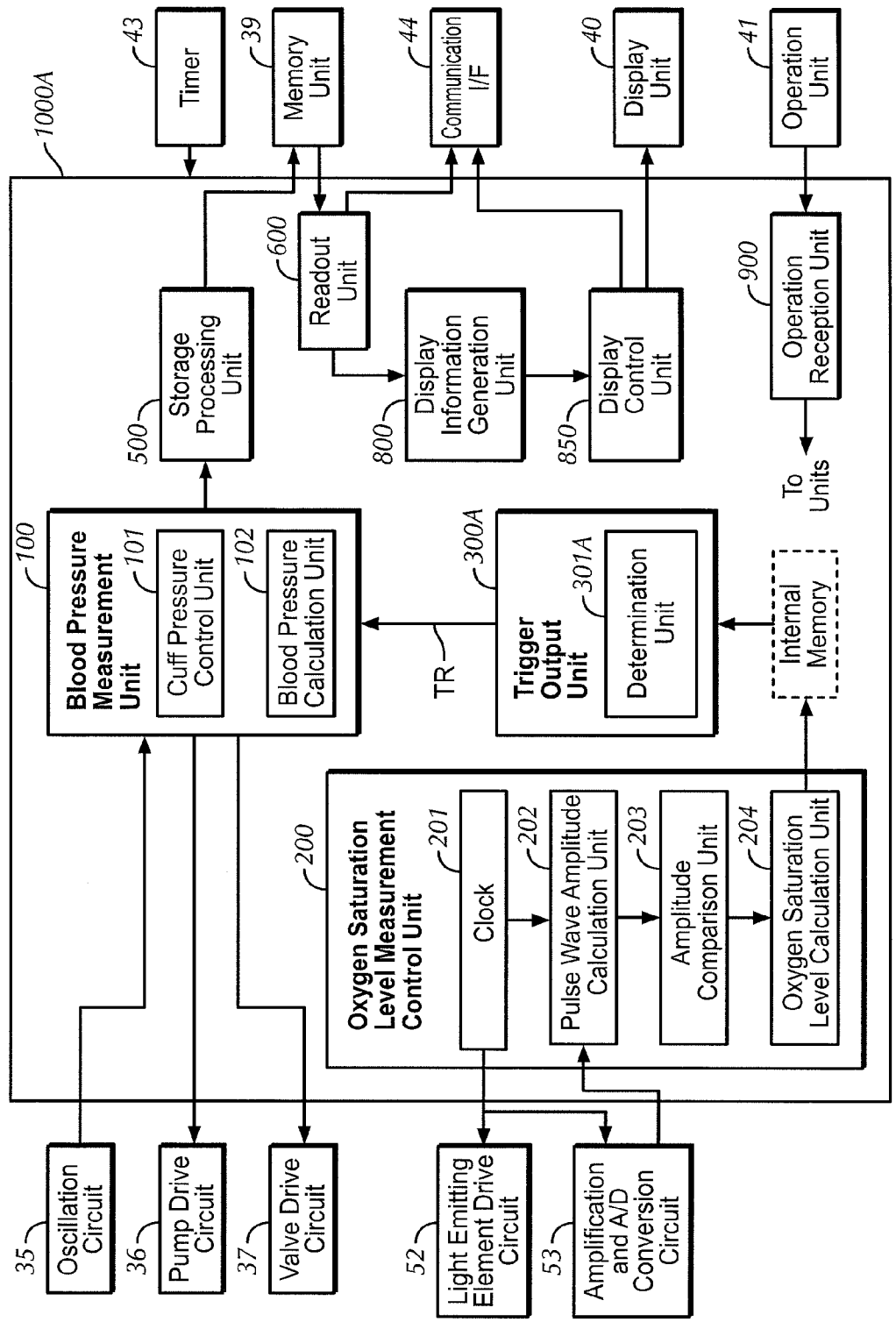
FIG. 3 shows a functional configuration of a blood pressure measurement apparatus according to Embodiment 1 of the present invention.

FIG. 3 shows the functional configuration of the blood pressure measurement apparatus 1A according to Embodiment 1 of the present invention. FIG. 3 shows the functional configuration of the CPU 1000A of the blood pressure measurement apparatus 1A along with circuits in the periphery thereof. As shown in FIG. 3, the CPU 1000A includes the following: a blood pressure measurement unit 100; an oxygen saturation level measurement control unit 200 that has an oxygen saturation level calculation unit 204 that functions as an information acquisition unit for acquiring an oxygen saturation level as information related to blood pressure variation; a trigger output unit 300A that outputs a trigger TR to the blood pressure measurement unit 100; a storage processing unit 500 for storing data in the memory unit 39; a readout unit 600 for reading out data from the memory unit 39; a display information generation unit 800 that has a VRAM (Video Random Access Memory) or the like for generating display information to be displayed on the display unit 40; a display control unit 850 that has a digital signal processing circuit or the like for controlling the display on the display unit 40; and an operation reception unit 900 that receives user operations performed using the operation unit 41 and outputs instructions (commands) corresponding to the operations to various units. These units are configured using programs and data stored in the memory unit 39 and/or circuit modules.

The oxygen saturation level measurement control unit 200 has the oxygen saturation level calculation unit 204, which functions as an information acquisition unit for acquiring an oxygen saturation level as information related to blood pressure variation.

The trigger output unit 300A includes a determination unit 301A for determining whether or not the oxygen saturation level satisfies a predetermined condition, and has a function of starting the blood pressure measurement unit 100 and causing blood pressure measurement to be executed with use of a trigger TR.

The blood pressure measurement unit 100 includes a cuff pressure control unit 101 and a blood pressure calculation unit 102. The cuff pressure control unit 101 adjusts the cuff pressure in the cuff 20 by controlling the operations of the pump drive circuit 36 and the valve drive circuit 37. The blood pressure measurement unit 100 receives an output signal from the oscillation circuit 35, detects the oscillation frequency of the received signal, and converts the detected oscillation frequency into a pressure value signal. The blood pressure measurement unit 100 includes an HPF (High Pass Filter) unit that extracts and outputs a volume pulse wave signal by performing HPF processing on the pressure value signal, and an LPF (Low Pass Filter) unit that extracts and outputs a pressure absolute value signal (referred to hereinafter as the "cuff pressure signal") by performing LPF processing on the pressure value signal.

The blood pressure calculation unit 102 receives the volume pulse wave signal that was extracted by the HPF unit, and performs processing on the received volume pulse wave signal in accordance with a predetermined procedure so as to calculate a maximum blood pressure (SBP (Systolic Blood Pressure)) and a minimum blood pressure (DBP (Diastolic Blood Pressure)), and also calculates the pulse rate in accordance with a known procedure. The blood pressure calculation procedure is envisioned to conform to an oscillometric method, in which pressure is applied to the measurement site by the cuff 20 up to a predetermined pressure, and the blood pressure is measured based on the cuff pressure that is detected as the pressure is then gradually reduced, but there is no limitation to the calculation method.

The oxygen saturation level measurement control unit 200 includes a clock 201 that outputs a clock signal that is synchronized with the time output by the timer 43, a pulse wave amplitude calculation unit 202, a pulse wave amplitude comparison unit 203, and the oxygen saturation level calculation unit 204.

The oxygen saturation level measurement control unit 200 controls the light emitting element drive circuit 52 at a timing defined by the clock 201 such that the light emitting elements 501 and 502 alternatingly emit two wavelengths of infrared light. Infrared light that passes through the subject measurement site and arrives at the light receiving element 503 is detected by the light receiving element 503. At that time, variation in arterial volume that accompanies pulsation of the intra-arterial pressure is reflected as change in the amount of transmitted light in the output from the light receiving element 503. This is called a photoelectric pulse wave (referred to hereinafter as simply "pulse wave"). When pulse wave signals are sent from the light receiving element 503 to the amplification and A/D conversion circuit 53, the pulse waves for different wavelengths are separately amplified and subjected to A/D conversion at a timing defined by the clock 201. The A/D converted pulse wave signals are then sent to the pulse wave amplitude calculation unit 202.

The pulse wave amplitude calculation unit 202 detects, in units of beats, the pulse waves obtained by the amplification and A/D conversion circuit 53, and calculates the amplitudes of the respective pulse waves. The pulse wave amplitude comparison unit 203 obtains the ratio of the amplitudes of the two wavelengths of pulse waves that were calculated by the pulse wave amplitude calculation unit 202. The oxygen saturation level calculation unit 204 calculates the oxygen saturation level in the blood based on the pulse wave amplitude ratio that was calculated. The oxygen saturation level calculation unit 204 then calculates the blood oxygen saturation level of the subject based on a relationship between pulse wave amplitude ratios and oxygen saturation levels that is stored in the memory unit 39 in advance.

The blood oxygen saturation level is calculated every five seconds, for example, and the calculated blood oxygen saturation levels are stored in a time-series that conforms to the order of measurement, beginning with the head address in an internal memory of the CPU 1000A. A pointer variable i is used to indicate blood oxygen saturation levels in the internal memory. The internal memory is then initialized when measurement ends.

In the present embodiment, the light emitting elements 501 and 502, the light receiving element 503, the light emitting element drive circuit 52, the amplification and A/D conversion circuit 53, and the oxygen saturation level measurement control unit 200 function as an oxygen saturation level measurement unit for measuring the blood oxygen saturation level. Note that the configuration of the oxygen saturation level measurement unit and the method of calculating the blood oxygen saturation level that are employed in the blood pressure measurement apparatus 1A according to the present invention are not intended to be limited to those described above.

Memory Configuration

Figures 4, 5:
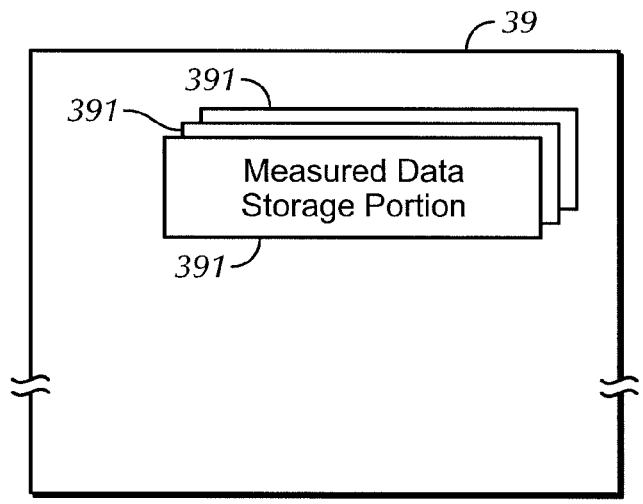
FIG. 4 is a diagram showing an example of content in a memory unit according to Embodiment 1 of the present invention.
FIG. 5 is a diagram showing an example of content in measured data storage portions according to Embodiment 1 of the present invention.

FIG. 4 is a diagram showing an example of content in the memory unit 39 according to Embodiment 1 of the present invention. As shown in FIG. 4, the memory unit 39 has a measured data storage portion 391 for each subject. FIG. 5 is a diagram showing an example of content in the measured data storage portions 391 according to Embodiment 1 of the present invention.

As shown in FIG. 5, the measured data storage portions 391 store measured data in a database format. Specifically, ID data for uniquely identifying the corresponding subject, and one or more records R are stored. Each record R includes No. data for uniquely identifying the record, time data indicating the measurement time, as well as a blood oxygen saturation level SpO2, a systolic blood pressure SBP, a diastolic blood pressure DBP, and a pulse rate PL that were measured (or calculated) at that measurement time.

Although these types of data are stored in association with each other using the records R in FIG. 5, they are not limited to a storage format that uses the records R, as long as they can be associated with each other.

Flowchart

Figure 6:
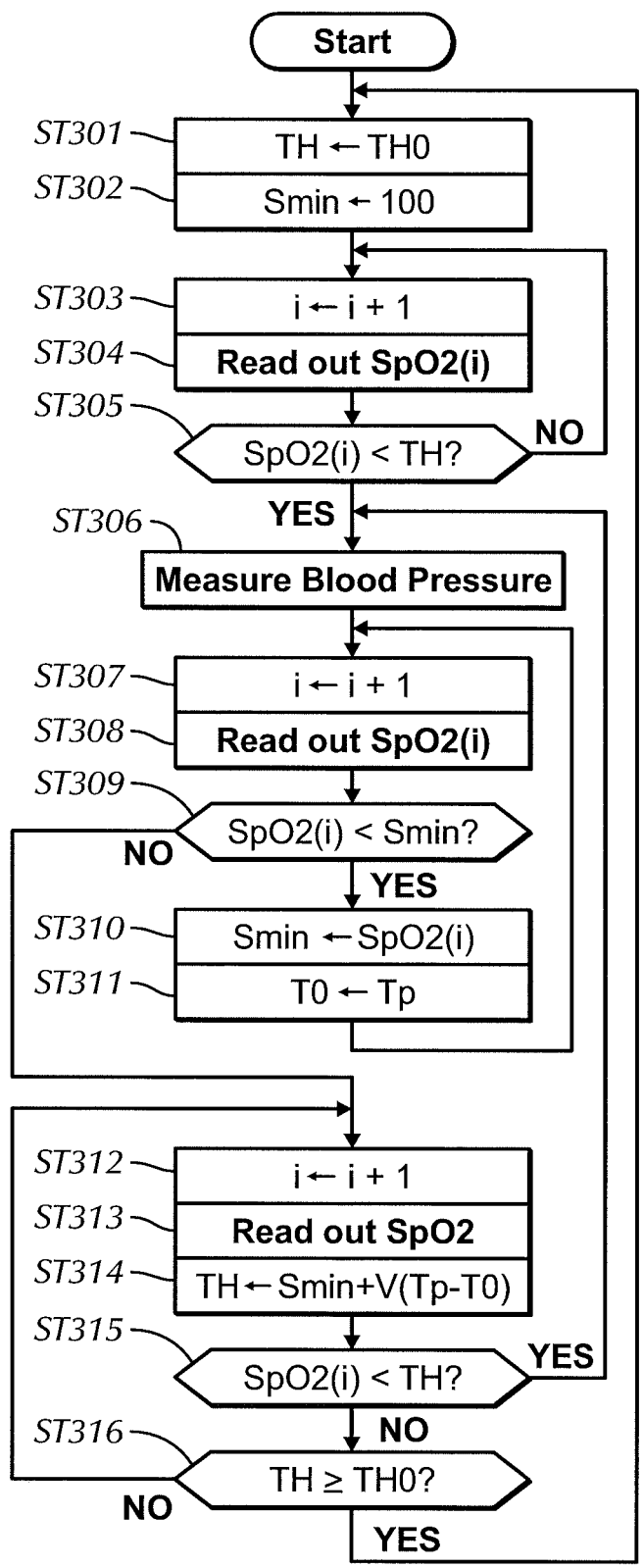
FIG. 6 is a flowchart of measurement processing according to Embodiment 1 of the present invention.

FIG. 6 is a flowchart of measurement processing according to Embodiment 1 of the present invention. A program that conforms to this flowchart is stored in advance in a predetermined storage area of the memory unit 39, and functionality that conforms to this processing flowchart is realized by the CPU 1000A reading out that program from the memory unit 39 and executing it. Although the measurement period is the sleep period here, the measurement period is not limited to the sleep period, and may be any period in which an apneic state can arise.

When measurement is to be performed, it is envisioned that the cuff 20 and the sensor unit 50 will be fitted at respective measurement sites on the subject. Before sleeping, the subject powers on the blood pressure measurement apparatus 1A, operates a switch for instructing the start of measurement, and operates a switch for instructing the end of measurement upon getting up.

The CPU 1000A starts performing processing upon receiving the measurement start instruction as a result of the switch operation for starting measurement. The CPU 1000A monitors whether a measurement end instruction has been input as a result of a switch operation during processing as well. If an end instruction is input, processing is forcibly ended even if processing is being executed.

When processing is started, the trigger output unit 300A sets a variable T0 to the value of 0, and sets a threshold value TH for evaluating the blood oxygen saturation level to an initial value TH0. It is desirable that the value of the initial value TH0 is set such that the blood oxygen saturation level falls below it even with a mild OSA sufferer who only exhibits mild apnea attacks, such as being set to around 90% (step ST301). Next, a variable Smin for storing the minimum value of the blood oxygen saturation level is set to the physiological upper limit of 100 (percent) (step ST302). Note that the blood oxygen saturation level measured for the subject is envisioned to be less than or equal to this physiological upper limit value (100%).

The trigger output unit 300A increments, by 1, the value of the variable i for indicating the blood oxygen saturation level in the time-series in the internal memory (step ST303), reads out the blood oxygen saturation level stored at the address indicated by the variable i from the internal memory, and sets the readout blood oxygen saturation level as the variable SpO2(i) (step ST304).

The determination unit 301A of the trigger output unit 300A determines whether or not the value of the blood oxygen saturation level indicated by the variable SpO2(i) is lower than the threshold value TH (step ST305). If it is determined that the blood oxygen saturation level is lower (YES in step ST305), the procedure moves to the processing of step ST306, and if it is determined that the blood oxygen saturation level is not lower (NO in step ST305), the procedure returns to step ST303, and the processing of steps ST303 to ST305 is repeated.

If it is determined that the value of the blood oxygen saturation level is lower than the threshold value TH, the trigger output unit 300A outputs the trigger TR to the blood pressure measurement unit 100. Upon receiving the trigger TR, the blood pressure measurement unit 100 is started, and blood pressure measurement is performed (step ST306).

Measured data is then stored in a measured data storage portion 391 via the storage processing unit 500.

Next, the trigger output unit 300A increments the variable i by 1 (step ST307), reads out the next blood oxygen saturation level indicated by the variable i from the internal memory, and sets the readout blood oxygen saturation level as the variable SpO2(i) (step ST308). Next, it is determined whether the value of the blood oxygen saturation level indicated by the variable SpO2 is lower than the value of the variable Smin (step ST309). If it is determined that the blood oxygen saturation level is lower (YES in step ST309), the value of the variable Smin is updated (step ST310). Specifically, the variable Smin is set to the value of the blood oxygen saturation level indicated by the variable SpO2(i) (step ST310), the variable T0 is set to the value of a variable Tp (step ST311), and then the procedure returns to step ST307, and the processing of steps ST307 to ST311 is repeated. Note that the value of the variable Tp is constantly updated using time data output by the timer 43. Accordingly, the variable Tp represents the current time.

On the other hand, if it is determined that the value of the blood oxygen saturation level indicated by the variable SpO2(i) is not less than the value of the variable Smin (NO in step ST309), it is determined that the blood oxygen saturation level of the subject has started to move to a process of rising. In other words, it is detected that the blood oxygen saturation level reached the local minimum value in the processing of changing in the time-series. When the local minimum value is detected, the trigger output unit 300A increments the variable i by 1 (step ST312), reads out the next blood oxygen saturation level indicated by the variable i from the internal memory, and sets the variable SpO2(i) to the readout blood oxygen saturation level (step ST313). The trigger output unit 300A then updates the threshold value TH in accordance with the equation TH=Smin+V(Tp−T0) (step ST314). In this way, the threshold value TH is calculated (updated) using a feature value (i.e., local minimum value) extracted in the process in which the blood oxygen saturation level changes in the time-series.

Next, the determination unit 301A of the trigger output unit 300A determines whether or not the value of the variable SpO2(i) is lower than the threshold value TH (step ST315). If it is determined that the value of the variable SpO2(i) is lower (YES in step ST315), the procedure returns to step ST306 and processing is executed from that step, and if it is determined that the value of the variable SpO2(i) is not lower (NO in step ST315), the threshold value TH and the initial value TH0 are compared (step ST316). If it is determined based on the result of the comparison that the threshold value TH is higher than or equal to the initial value TH0 (YES in step ST316), the procedure returns to step ST301, and processing is repeated from that step. If it is determined that the threshold value TH is lower than the initial value TH0 (NO in step ST316), the procedure returns to step ST312, and processing is performed from that step.

Update of Threshold Value TH

The following describes a calculation equation for updating the threshold value TH in step ST314.

In the present embodiment, operations are realized such that during a relatively short period of elapsed time from when the previous (most recent) blood pressure measurement started, blood pressure measurement is not started in the case of hypoxia similar in extent to that when blood pressure measurement was previously performed, and then if a relative long period elapses, blood pressure measurement is started even in the case of a lower extent of hypoxia than that when blood pressure measurement was previously performed. In other words, even in the case of a relatively low extent of hypoxia, blood pressure measurement is started if a long time has elapsed from when the previous blood pressure measurement was started. That is to say, the longer the elapsed time is, the greater the amount of change when the threshold value is updated. For this reason, in the present embodiment, the threshold value TH for the blood oxygen saturation level (variable SpO2(i)) for starting blood pressure measurement is determined using the equation in step ST314.

Here, the variable V in the equation represents the rate of change of threshold value per hour, and is set to 10 (%/hr) for example. Also, in the equation, the variable Tp represents the current time, and the variable T0 represents the time when the previous blood pressure measurement was started. Also, according to this equation, if the threshold value TH is higher than or equal to the initial value TH0 (90%), the initial value TH0 is set as the threshold value TH. Note that although the time-dependent function is a linear function of time, the function is not limited to this form.

In Embodiment 1, the threshold value TH for determining whether or not to start blood pressure measurement is successively re-set using the lowest (local minimum value) blood oxygen saturation level of the subject. Also, as long as the lowest blood oxygen saturation level (variable Smin) is not updated, the threshold value TH is raised in a time-dependent manner in accordance with the above-described equation. Accordingly, after a long time has elapsed from when the previous blood pressure measurement started, blood pressure measurement can be started even if the mildly hypoxic blood oxygen saturation level is higher than the lowest blood oxygen saturation level (variable Smin). As a result, even if the lowest blood oxygen saturation level is measured relatively at the beginning of the period from when measurement starts until when it ends, blood pressure measurement can still be performed thereafter, and it is possible to acquire blood pressure measurement data over the entirety of the measurement period (e.g., the sleep period of the subject).

Rate of Change of Threshold Value TH

Figure 7:
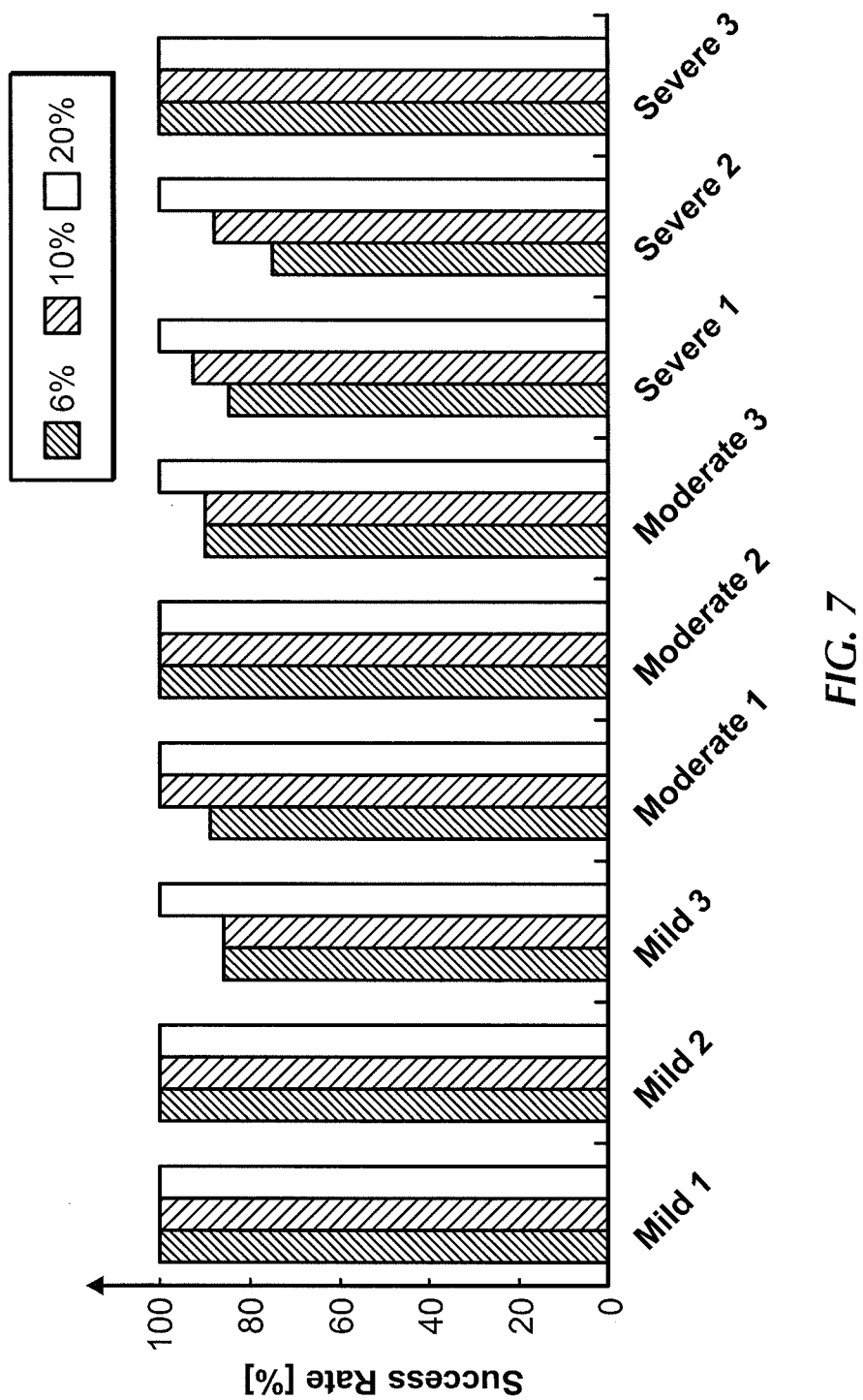
FIG. 7 is a graph for describing the rate of change of threshold value according to Embodiment 1 of the present invention.
Figure 8:
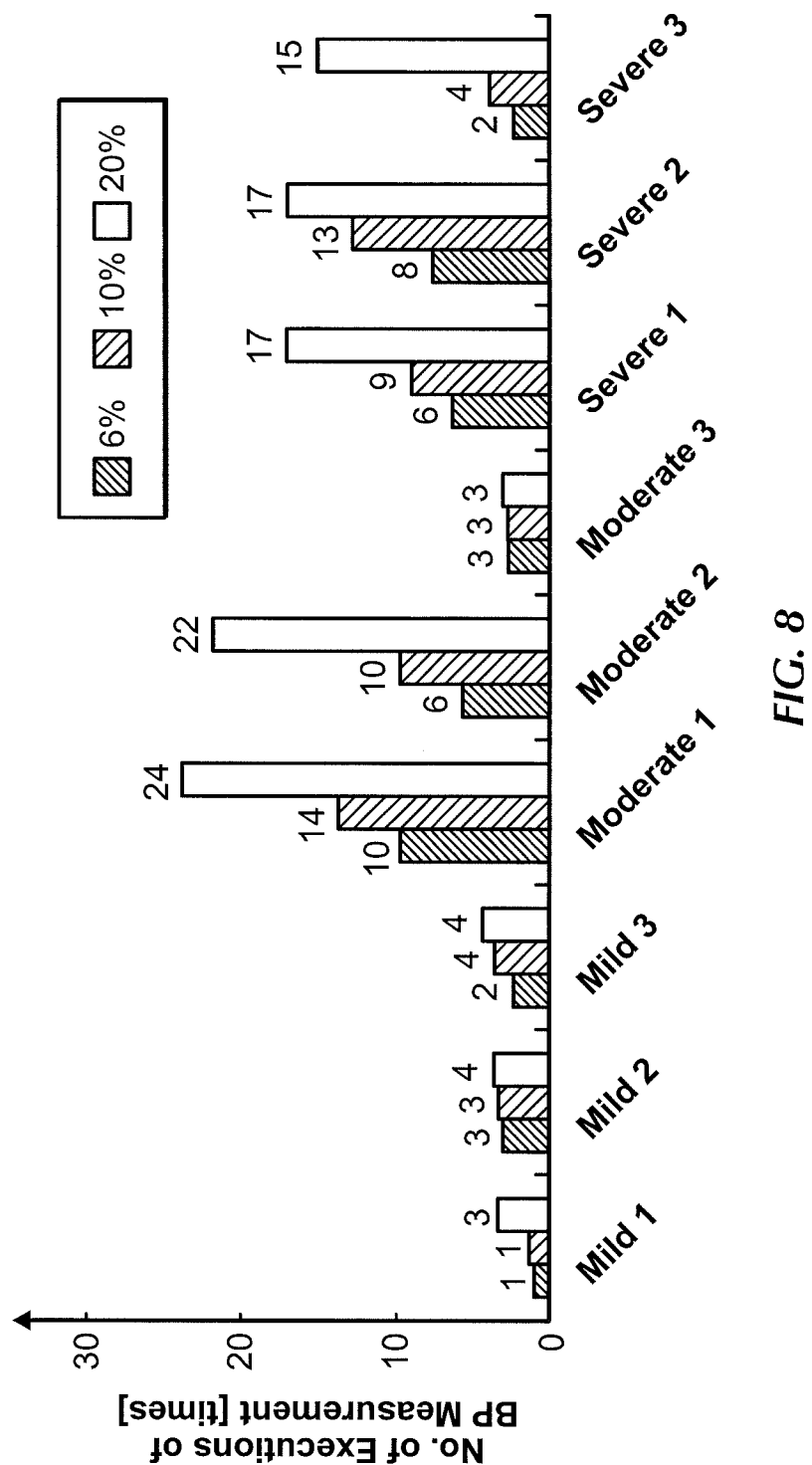
FIG. 8 is a graph for describing the rate of change of threshold value according to Embodiment 1 of the present invention.

FIGS. 7 and 8 are graphs for describing the rate of change of the threshold value according to Embodiment 1 of the present invention. The variable V in the equation of above-described step ST314 represents the rate of change of the threshold value TH (referred to hereinafter as the "RCOT"). FIGS. 7 and 8 show the results of a simulation performed by the inventors using the blood pressure measurement apparatus 1A. Based on the results, the rate of change of the threshold value TH was determined to be 10% per hour.

In this simulation, data on the blood oxygen saturation level measured from 9 people (3 patients with mild OSA, 3 patients with moderate OSA, and 3 patients with severe OSA) was used to simulate the execution of operations for starting blood pressure measurement with the RCOT set to 6%, 10%, and 20%.

First, an apnea attack in which blood pressure measurement should be performed (necessary point) and an apnea attack in which blood pressure measurement should be skipped (unnecessary point) were designated in the actual data on the blood oxygen saturation level obtained from the 9 people. The conditions for the necessary point were that the attack is an attack that is accompanied by a blood oxygen saturation level that is the lowest in one night, and that the attack is an attack that is accompanied by a substantially equivalent reduction in blood oxygen saturation level after a long period of 3 hours or more after the minimum blood oxygen saturation level was measured. The conditions for the unnecessary point were that the attack is an apnea attack that is not a long time after the necessary point, regardless of the amount of reduction in the blood oxygen saturation level. The simulation was performed for designated apnea attacks at a total of 114 points (82 necessary points and 32 unnecessary points) with the RCOT set to 6%, 10%, and 20%. The success rate was defined as the frequency of operation as designated (i.e., detection at a necessary point and skipping at an unnecessary point), and evaluation was performed for each RCOT with the allowable range of 90% or more. As a result, the success rates for the RCOTs of 6%, 10%, and 20% at the necessary points were 86.6%, 95.1%, and 100.0% respectively (see FIG. 7). The success rate at the unnecessary points was 100.0% for all of the RCOTs. Accordingly, it was found that 10% and 20% would be appropriate as the value of the RCOT evaluated based on the success rate.

Next, the number of executions of blood pressure measurement per night was evaluated. Although many apnea attacks other than those at designated points appeared in the data on the blood oxygen saturation level measured from the 9 people, the number of executions of blood pressure measurement per night was considered to be 15 or less from a practical point of view. The reason for this is that with ambulatory blood pressure monitoring (ABPM), which is currently widely used for blood pressure measurement during nocturnal sleep, the measurement frequency per hour is generally often set to 2, and therefore the number of executions of measurement per night will be 15 to 16 when envisioning a sleep period of 8 hours.

The results of the simulation performed using the RCOTs of 6%, 10%, and 20% were that the number of subjects on which blood pressure measurement was executed 15 times or more was 0 people, 0 people, and 5 people (56%) respectively (see FIG. 8). Accordingly, it was found that 6% and 10% are appropriate as the value of the RCOT evaluated based on blood pressure measurement. Based on the results of the two simulations described above, the inventors employed 10% as the most appropriate value for the rate of change of threshold value (variable V).

Comparison with Threshold Value (Fixed)

Figure 9:
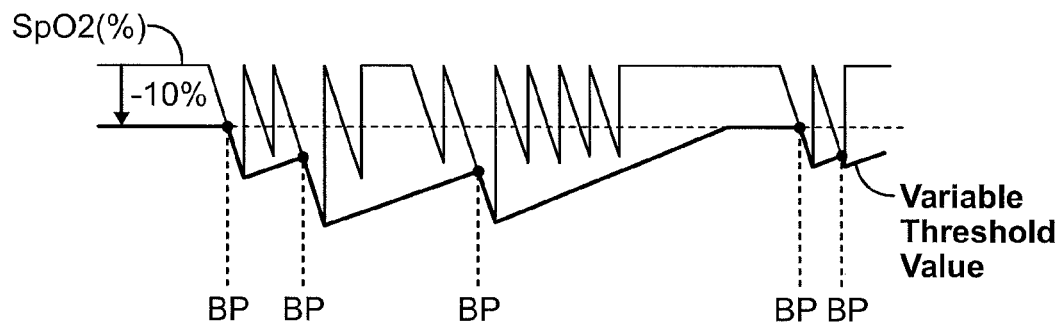
FIG. 9 is a graph for describing measurement with a variable threshold value according to Embodiment 1 of the present invention.
Figure 10A:
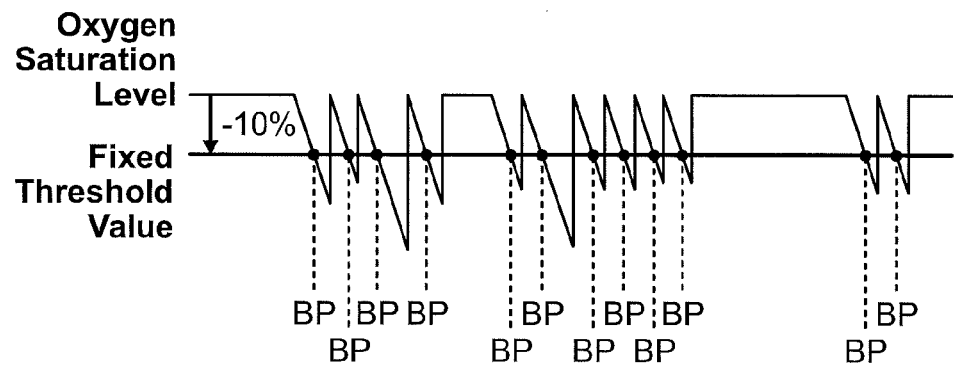
FIGS. 10A and 10B are graphs for describing measurement with a variable threshold value according to Embodiment 1 of the present invention, in comparison to measurement with a fixed threshold value.
Figure 10B:
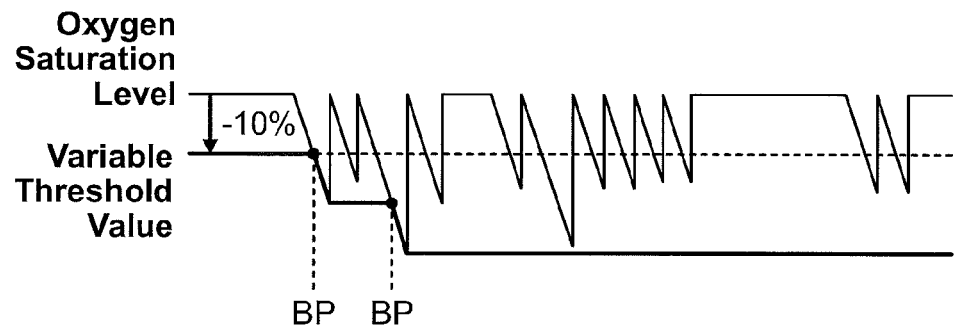

FIGS. 9, 10A, and 10B are graphs for describing measurement with a variable threshold value according to Embodiment 1 of the present invention, in comparison to measurement with a fixed threshold value. FIGS. 9, 10A, and 10B show the association between change in the blood oxygen saturation level measured in accordance with the elapse of measurement time and the timing of blood pressure measurement start BP for the same subject.

FIG. 9 shows the case of Embodiment 1, in which the threshold value TH is variably set using the rate of change of threshold value V over the measurement period. FIG. 9 shows that due to the threshold value being calculated using a feature value extracted in the process in which the blood oxygen saturation level SpO2 changes in the time-series, that is to say, using a local minimum value (step ST314), blood pressure measurement is performed both when the blood oxygen saturation level is relatively low and when it is relatively high, that is to say, over the entirety of the measurement period. In contrast, FIG. 10A shows the case where the threshold value is fixed (not changed) as in conventional technology, and this graph shows that blood pressure measurement is started each time hypoxia occurs, and therefore blood pressure measurement is performed a very large number of times. FIG. 10B shows the case of a method in which the threshold value is updated using the lowest blood oxygen saturation level, and it can be seen that if the largest reduction in the blood oxygen saturation level occurs in the initial stage of the measurement period, blood pressure measurement will not be performed thereafter. Accordingly, according to Embodiment 1, blood pressure measurement is started when the blood oxygen saturation level is low, and blood pressure measurement data can be acquired over the entirety of the measurement period (e.g., the sleep period of the subject).

Comparison with ABPM

Figure 11:
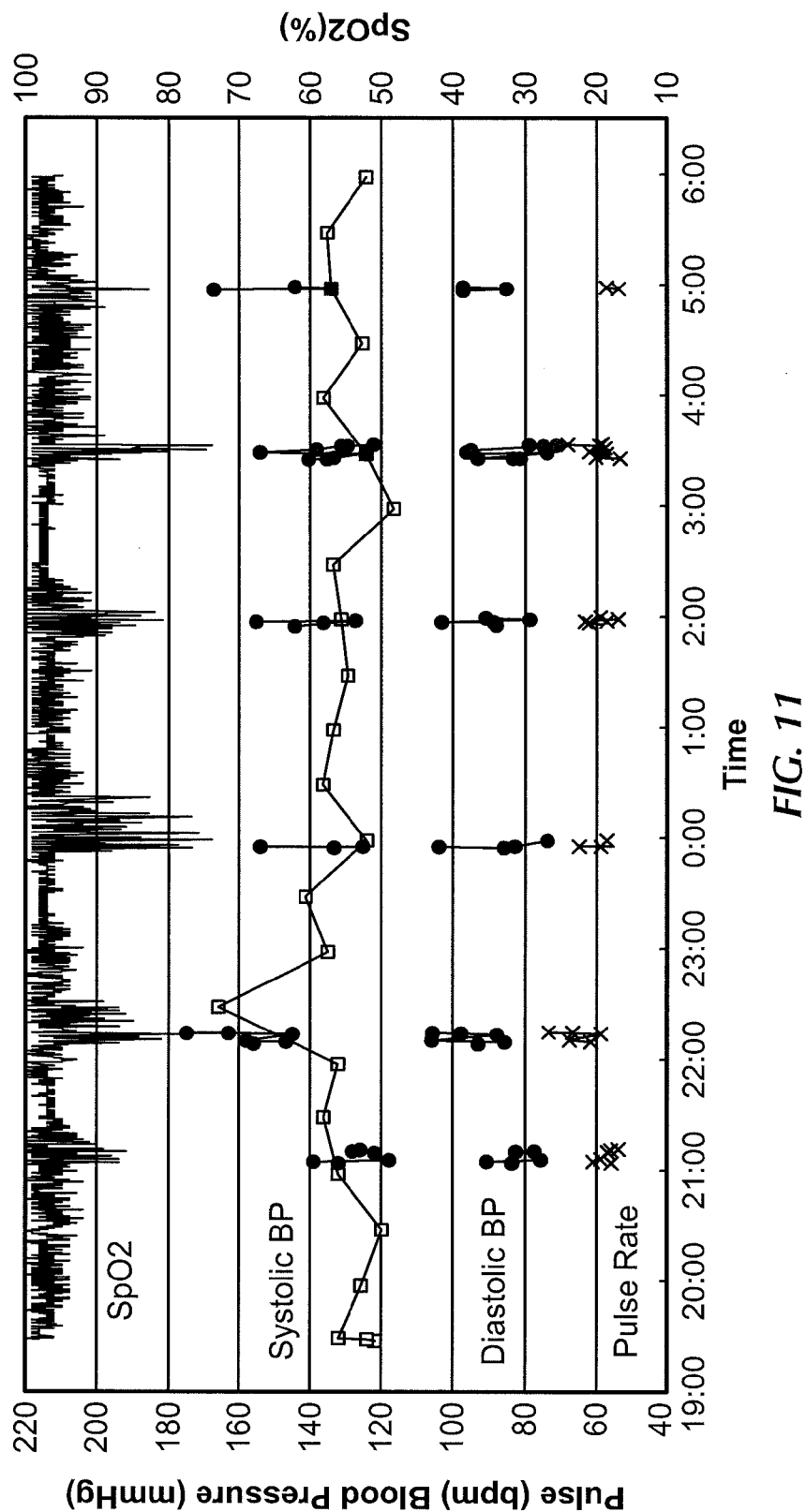
FIG. 11 is a graph for describing measurement with a variable threshold value according to Embodiment 1 of the present invention, in comparison to measurement by ABPM.

FIG. 11 is a graph for describing measurement with a variable threshold value according to Embodiment 1 of the present invention, in comparison to measurement by ABPM. This graph was obtained by experimentation performed by the inventors. The top level in FIG. 11 shows change in the blood oxygen saturation level measured in the sleep period of the subject (19:00 to 6:00). In ABPM, blood pressure measurement is performed 2 times per hour. The line graph in this figure shows change in the blood pressure (systolic blood pressure SBP) measured using ABPM. According to ABPM, the blood pressure is measured at a constant interval, regardless of change in the blood oxygen saturation level, and therefore it is understood that blood pressure measurement is not performed in synchronization with the timing of a reduction in the blood oxygen saturation level.

In contrast, in the case of performing measurement with the blood pressure measurement apparatus 1A of Embodiment 1, blood pressure measurement is started each time the blood oxygen saturation level decreases, as shown by the black circles plotted in the graph, and it is understood that as a result of this, measured data (systolic blood pressure SBP, diastolic blood pressure DBP, and pulse rate) can be acquired in synchronization with the timing of a reduction in the blood oxygen saturation level.

Embodiment 2

The blood oxygen saturation level of a subject is dependent on the subject's respiratory pattern. In view of this, in Embodiment 2, the subject's respiration is monitored, and the blood pressure measurement unit is started based on change in respiration (inhalation and exhalation) in a time-series obtained as a result of the monitoring.

Blood Pressure Measurement Apparatus

Figure 12:
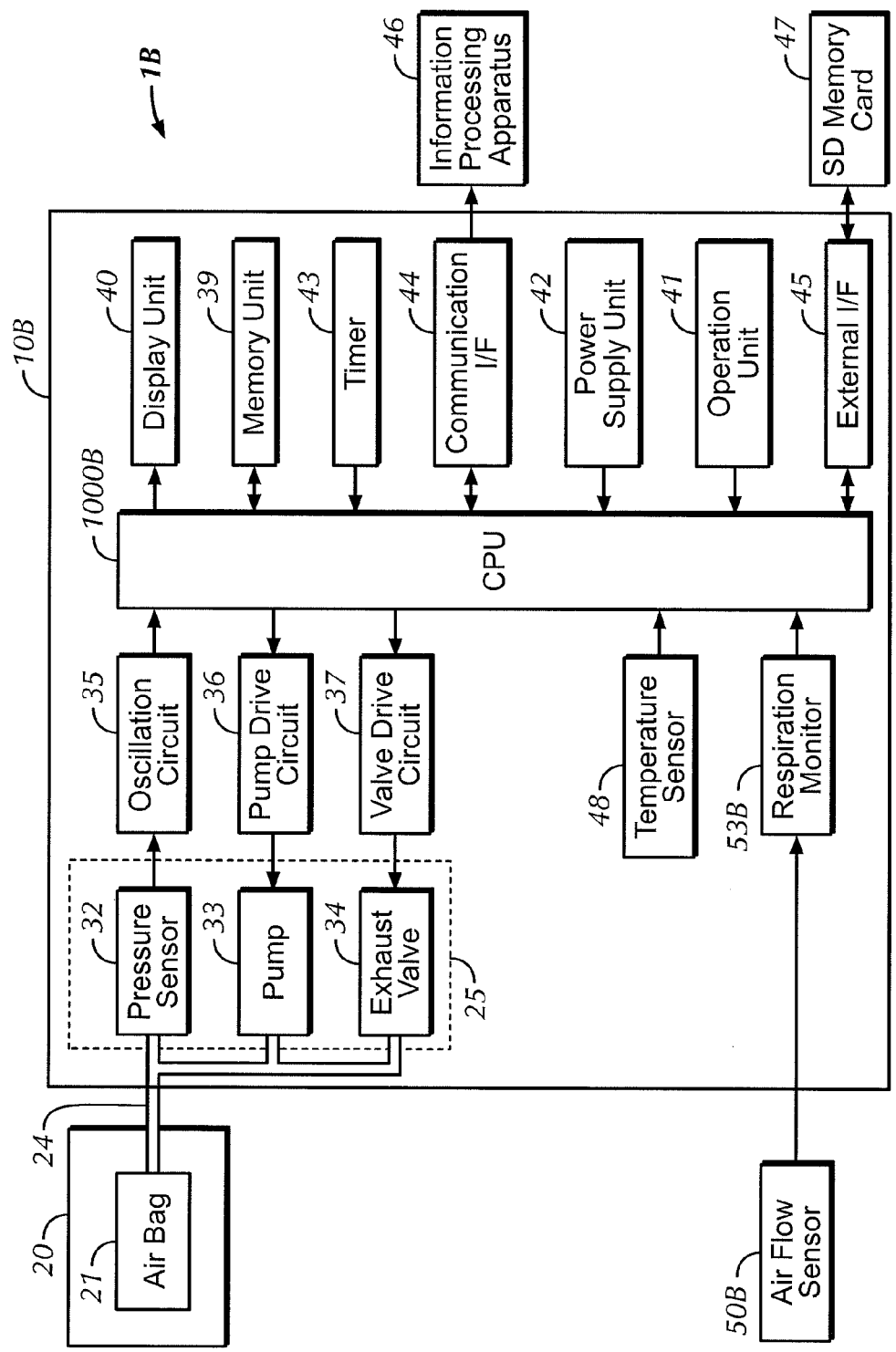
FIG. 12 shows a hardware configuration of a blood pressure measurement apparatus according to Embodiment 2 of the present invention.

FIG. 12 shows the hardware configuration of a blood pressure measurement apparatus 1B according to Embodiment 2 of the present invention. As shown in FIG. 12, the blood pressure measurement apparatus 1B and the blood pressure measurement apparatus 1A are different in that the blood pressure measurement apparatus 1B includes a body unit 10B in place of the body unit 10A and includes an airflow sensor 50B in place of the sensor unit 50 for measuring the blood oxygen saturation level. Other configurations of the blood pressure measurement apparatus 1B will not be described since they are similar to those of the blood pressure measurement apparatus 1A, and only the differences will be described below. Note that although a temperature sensor 48 for measuring the temperature around the blood pressure measurement apparatus 1B is provided in FIG. 12, details regarding the temperature sensor 48 will be described later since it is not an essential requirement for measurement according to Embodiment 2.

The body unit 10B includes a respiration monitor 53B in place of the light emitting element drive circuit 52 and the amplification and A/D conversion circuit 53, and includes a CPU 1000B in place of the CPU 1000A. Other configurations of the body unit 10B are the same as those of the body unit 10A, and redundant descriptions will not be given for them.

The respiration monitor 53B receives a detection signal from the airflow sensor 50B, monitors the respiratory state of the subject based on the received detection signal, and outputs a respiration signal indicating the monitoring results to the CPU 1000B.

Figure 13:
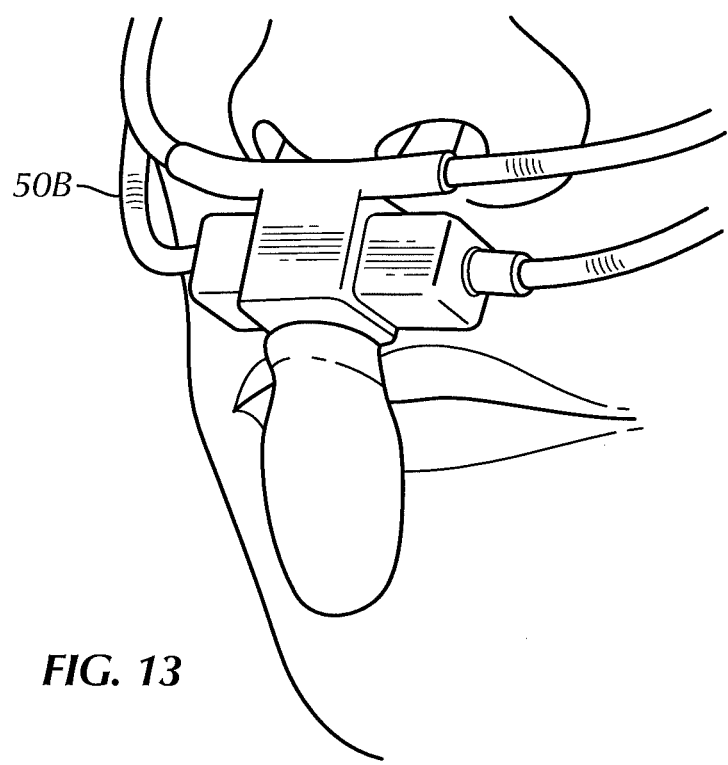
FIG. 13 is a diagram showing an external view of an airflow sensor according to Embodiment 2 of the present invention.

FIG. 13 is a diagram showing an external view of the airflow sensor 50B according to Embodiment 2 of the present invention. As shown in FIG. 13, the airflow sensor 50B is fixedly fitted in the vicinity of the subject's nasal cavity. The airflow sensor 50B detects the air pressure in the vicinity of the nasal cavity using a built-in pressure sensor (not shown), and outputs a detection signal. The air pressure in the vicinity of the nasal cavity decreases during inhalation, and increases during exhalation.

The respiration monitor 53B derives the pattern of change in air pressure in the vicinity of the nasal cavity based on the detection signal from the airflow sensor 50B, and detects inhalation and exhalation through the subject's nasal cavity based on the derived pattern of change. Specifically, patterns of change for normal inhalation and exhalation of a subject are stored in advance, and inhalation or exhalation is detected by performing pattern matching with the stored patterns of change and the pattern of change derived during measurement. The result of the detection is output to the CPU 1000B as the respiration signal. Here, the respiration signal is a voltage signal, for example, where a positive voltage signal is output in an inhalation period, and a negative voltage signal is output in an exhalation period. The respiration monitor 53B outputs a zero voltage signal in a period determined to be neither inhalation nor exhalation (i.e., an apneic period) as a result of the above-described pattern matching.

Note that it is envisioned that the CPU 1000B receives the respiration signal output by the respiration monitor 53B once every second, for example, that the respiration monitor 53B receives the detection signal from the airflow sensor 50B at a sufficiently shorter cycle than 1 sec, and that the airflow sensor 50B detects the air pressure at a cycle that is shorter than the reception cycle, and outputs the detection signal.

Figure 14:
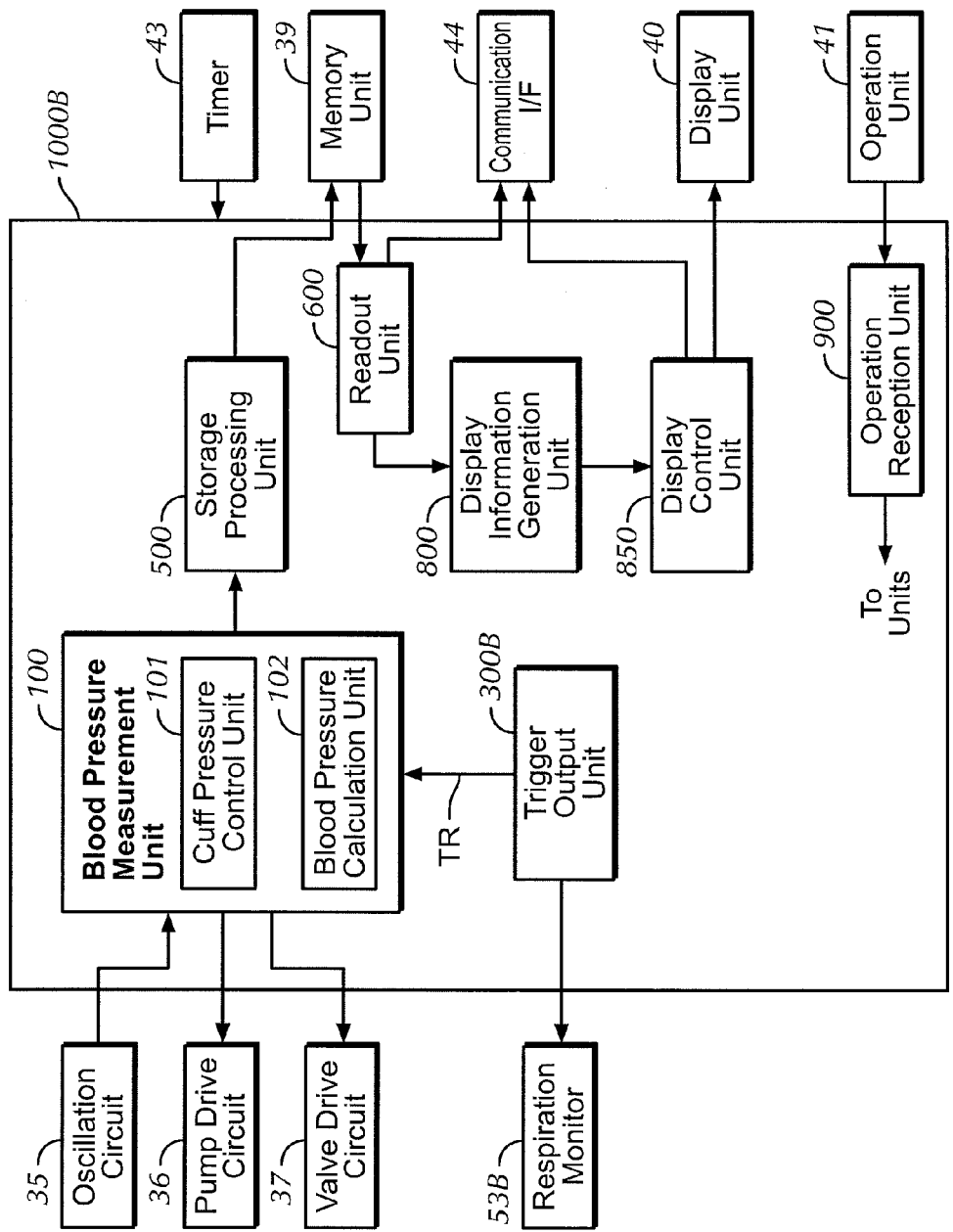
FIG. 14 shows a functional configuration of the blood pressure measurement apparatus according to Embodiment 2 of the present invention.

FIG. 14 shows the functional configuration of the blood pressure measurement apparatus 1B according to Embodiment 2 of the present invention. As shown in FIG. 14, the CPU 1000B and the CPU 1000A are different in that the CPU 1000B includes a trigger output unit 300B in place of the trigger output unit 300A. Other functions will not be described since they are the same as the functions of the CPU 1000A.

The trigger output unit 300B detects apnea based on the respiration signal from the respiration monitor 53B, and outputs the trigger TR for starting blood pressure measurement to the blood pressure measurement unit 100.

Trigger Output Based on Respiration

Figure 15:
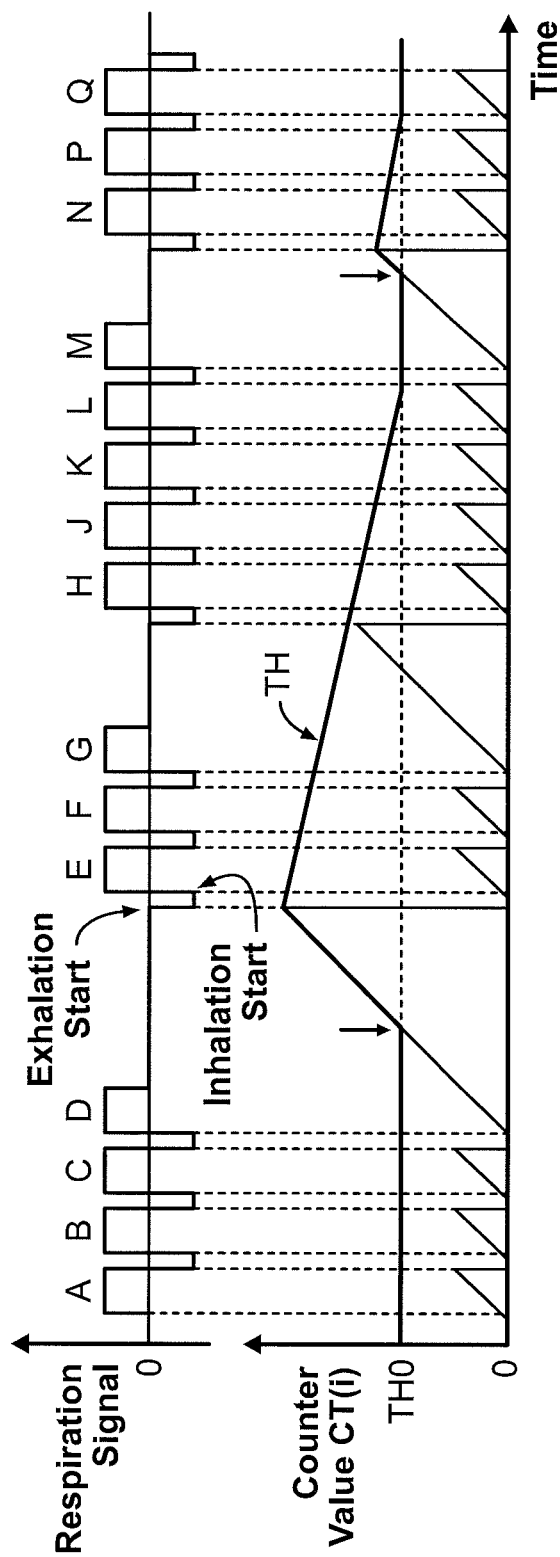
FIG. 15 is a timing chart showing a relationship between a respiration signal and trigger output according to an embodiment of the present invention.

FIG. 15 is a timing chart showing the relationship between the respiration signal and the output of the trigger TR according to this embodiment of the present invention. The trigger output unit 300B detects apnea upon detecting, based on the respiration signal, that the time period from when inhalation started until when the immediately subsequent exhalation starts is longer than a predetermined time period. In other words, when inhalation starts, the trigger output unit 300B starts a count up performed by a counter (not shown), and when exhalation starts, stops the count up performed by the counter and resets (initializes) the counter value. Note that the trigger output unit 300B performs the count up operation with the counter in synchronization with output from the timer 43.

The upper level in FIG. 15 shows a respiration signal that includes inhalation signals A to Q, and the lower level shows the counter value CT(i) that changes in synchronization with the respiration signal. Change in the threshold value TH is also shown in association with the counter value CT(i). The downward-facing arrows in FIG. 15 point to time points when blood pressure measurement started. As shown in FIG. 15, in normal periods in which apnea is not detected, such as the periods corresponding to the inhalation signals A to C, the counter value $CT(i)$ remains at a relatively low value, and then the next occurrence of inhalation starts. However, in an apneic period such as the period from inhalation corresponding to the inhalation signal D in FIG. 15 to the start of the immediately subsequent exhalation, the counter value $CT(i)$ rises to a very high value since exhalation does not occur in this period. The trigger output unit 300B changes the threshold value TH in accordance with the counter value $CT(i)$ that changes in this way.

As shown in the figure, the threshold value TH is first set to the initial value TH0 when measurement starts, and then when the counter value $CT(i)$ rises and exceeds the threshold value TH, the threshold value TH is updated so as to indicate the same value as the rising counter value $CT(i)$. The threshold value TH rises to the counter value $CT(i)$ up until the point in time when the apnea stops due to the start of subsequent exhalation. Thereafter, the threshold value TH decreases at a constant rate, and then the decrease stops at the point in time when the initial value TH0 is indicated.

In this way, the rate of increase and decrease of the threshold value TH is made variable, and therefore for a short while after severe apnea occurs such as immediately after the inhalation signal D, a similar level of apnea (apnea immediately after the inhalation signal G) is overlooked, and then when apnea occurs after a sufficient period of time has elapsed (apnea immediately after the inhalation signal M), blood pressure measurement is started even if it is mild apnea. In other words, the longer the elapsed time from blood pressure measurement, the greater the amount of change when the threshold value is updated.

Flowchart

Figure 16:
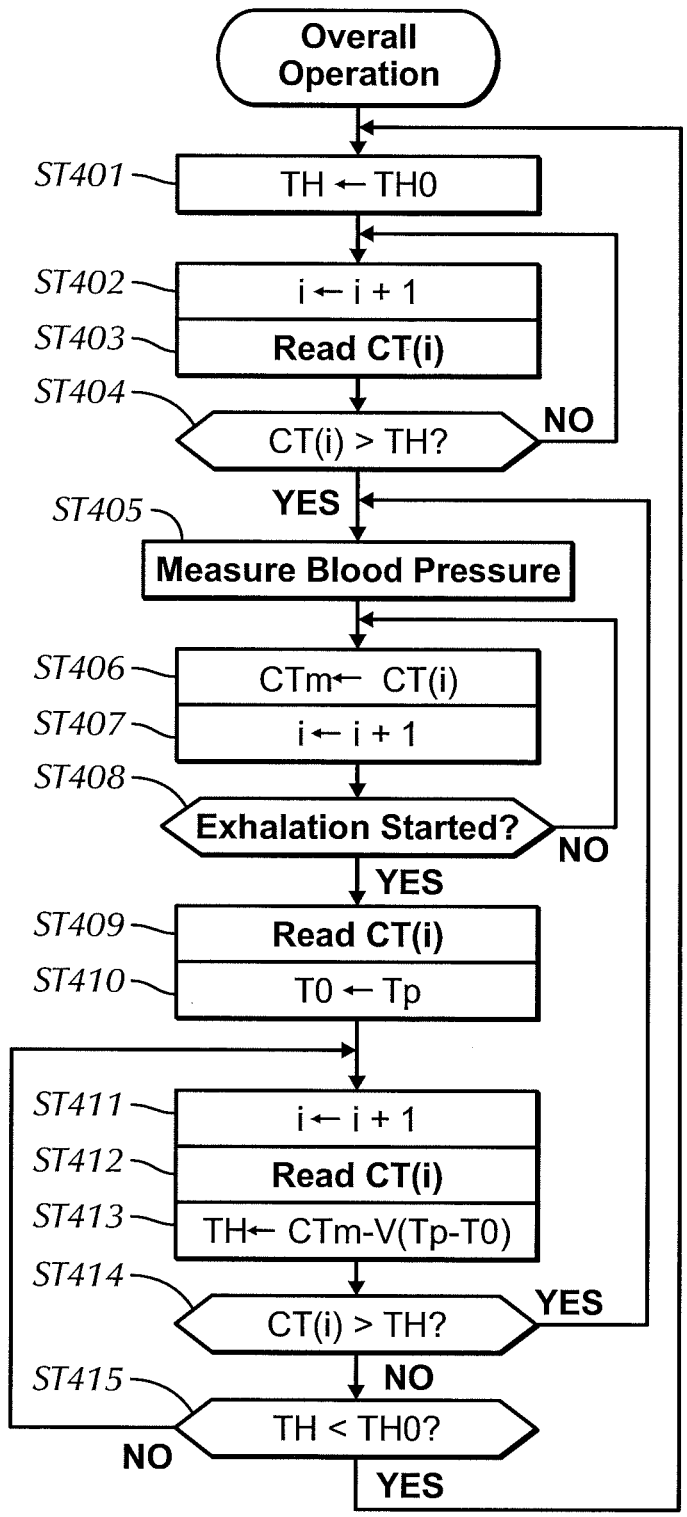
FIG. 16 is a flowchart of measurement processing according to Embodiment 2 of the present invention.

FIG. 16 is a flowchart of measurement processing according to Embodiment 2 of the present invention. A program that conforms to this flowchart is stored in advance in a predetermined storage area of the memory unit 39, and functionality that conforms to this processing flowchart is realized by the CPU 1000B reading out that program from the memory unit 39 and executing it. Although the measurement period is the subject's sleep period here, the measurement period is not limited to the sleep period, and may be any period in which an apneic state can arise.

When measurement is to be performed, it is envisioned that the cuff 20 and the airflow sensor 50B will be fitted at respective measurement sites on the subject. Before sleeping, the subject powers on the blood pressure measurement apparatus 1B, operates a switch for instructing the start of measurement, and operates a switch for instructing the end of measurement upon getting up.

The CPU 1000B starts performing processing upon receiving the measurement start instruction as a result of the switch operation for starting measurement. The CPU 1000B monitors whether a measurement end instruction has been input as a result of a switch operation during processing as well. If an end instruction is input, processing is forcibly ended even if processing is being executed.

When processing is started, the trigger output unit 300B sets the threshold value TH, which is for evaluating the length of the apneic period indicated by the value of the counter value $CT(i)$, to the initial value TH0 (step ST401). It is desirable that the initial value TH0 is set high enough to not be reached in a normal respiration cycle, and low enough to be reached in the case of a mild OSA sufferer who only exhibits mild apnea attacks, one example being the setting of approximately 15 seconds.

The value of the variable i indicating the signal time is then incremented by 1 (step ST402), and then the time from the timer 43 is set as the counter value $CT(i)$ that corresponds to the incremented variable i (step ST403).

Next, the trigger output unit 300B determines whether or not the counter value $CT(i)$ is higher than the threshold value TH (sec) (step ST404). If it is determined that the counter value $CT(i)$ is higher (YES in step ST404), the procedure moves to later-described step ST405, and if it is determined that the counter value $CT(i)$ is lower than or equal to threshold value TH (NO in step ST404), the procedure returns to step ST402, and the operations of steps ST402 to ST404 are repeated.

The trigger output unit 300B outputs the trigger TR upon determining that the counter value $CT(i)$ is higher than the threshold value TH. Accordingly, blood pressure measurement performed by the blood pressure measurement unit 100 is started (step ST405). The trigger output unit 300B also sets the counter value $CT(i)$ as a variable CTm, which is set to the maximum value of the counter value (step ST406), and increments the value of the variable i by 1 (step ST407).

Thereafter, it is determined whether exhalation by the subject has started, based on the respiration signal (step ST408). If it is determined that exhalation has not started (NO in step ST408), the procedure returns to step ST406, and processing is repeated from that step. On the other hand, if it is determined that exhalation has started (YES in step ST408), the counter value $CT(i)$ is set as the variable CTm (step ST409). The value of the variable Tp, which indicates the current time output by the timer 43 at that point in time, is set as the variable T0 (step ST410).

The trigger output unit 300B then increments the value of the variable i by 1 (step ST411), and sets the time from the timer 43 as the counter value $CT(i)$ that corresponds to the incremented variable i (step ST412). The threshold value TH is then re-set in accordance with the equation TH=CTm−V (Tp−T0) (step ST413), details of which will be described later.

Next, the trigger output unit 300B determines whether or not the counter value $CT(i)$ is higher than the threshold value TH (step ST414). If it is determined that the counter value $CT(i)$ is higher (YES in step ST414), the procedure returns to step ST405, and processing is repeated from that step. If it is determined that the counter value $CT(i)$ is lower than or equal to the threshold value TH (NO in step ST414), it is then determined whether or not the threshold value TH is lower than the initial value TH0 (step ST415). If it is determined that the threshold value TH is lower than the initial value TH0 (YES in step ST415), the procedure returns to step ST401, and processing is repeated from that step. If it is determined that the threshold value TH is higher than or equal to the initial value TH0 (NO in step ST415), the processing of steps ST411 to ST415 is repeated.

The following describes the equation used to update the threshold value TH in step ST413. In Embodiment 2, operations are realized such that if not very much time has elapsed from when the previous blood pressure measurement started, blood pressure measurement is not started when apnea continues for a duration similar to that when blood pressure measurement was previously performed, and then if a certain time period has elapsed, blood pressure measurement is started even if the apnea that occurs is more mild (the apneic period is shorter) than that when blood pressure measurement was previously performed. In other words, the determination of whether or not blood pressure measurement is to be started regardless of how mild the apnea is, is dependent on the amount of time that has elapsed from when the most recent (immediately previous) blood pressure measurement started.

In view of this, the aforementioned equation is used such that the updating of the threshold value TH that is referenced in order to start blood pressure measurement (the value for evaluating the length of the apneic period (value of the counter value CT(i)) is dependent on the amount of time that has elapsed from when blood pressure measurement started.

The variable V in the equation represents the rate of change of the threshold value TH per hour. Also, if the threshold value TH calculated by this calculation equation is less than the initial value TH0 (YES in step ST415), the initial value TH0 is set as the threshold value TH (step ST401). Note that although the time-dependent function is a linear function of time here as shown by the equation, the function is not limited to this form.

Embodiment 3

With a blood pressure measurement apparatus of Embodiment 3, attention is placed on the fact that the blood pressure changes rapidly when there is a change in the environmental temperature around the subject during measurement, and operations are performed such that, based on temperature data in a time-series obtained by measuring the ambient temperature, blood pressure measurement is executed after a certain time period has elapsed from when a rapid change in temperature occurred.

The blood pressure measurement apparatus of Embodiment 3 is configured such that the trigger output unit 300B of the blood pressure measurement apparatus 1B in FIG. 14 receives a temperature signal from the temperature sensor 48 instead of receiving a signal from the respiration monitor 53B. The temperature sensor 48 measures the environmental temperature around the blood pressure measurement apparatus 1B, and outputs a temperature signal to the trigger output unit 300B. The airflow sensor 50B of the blood pressure measurement apparatus 1B is removably attached to the apparatus. When the airflow sensor 50B is not attached, the trigger output unit 300B receives the temperature signal from the temperature sensor 48.

Figure 17:
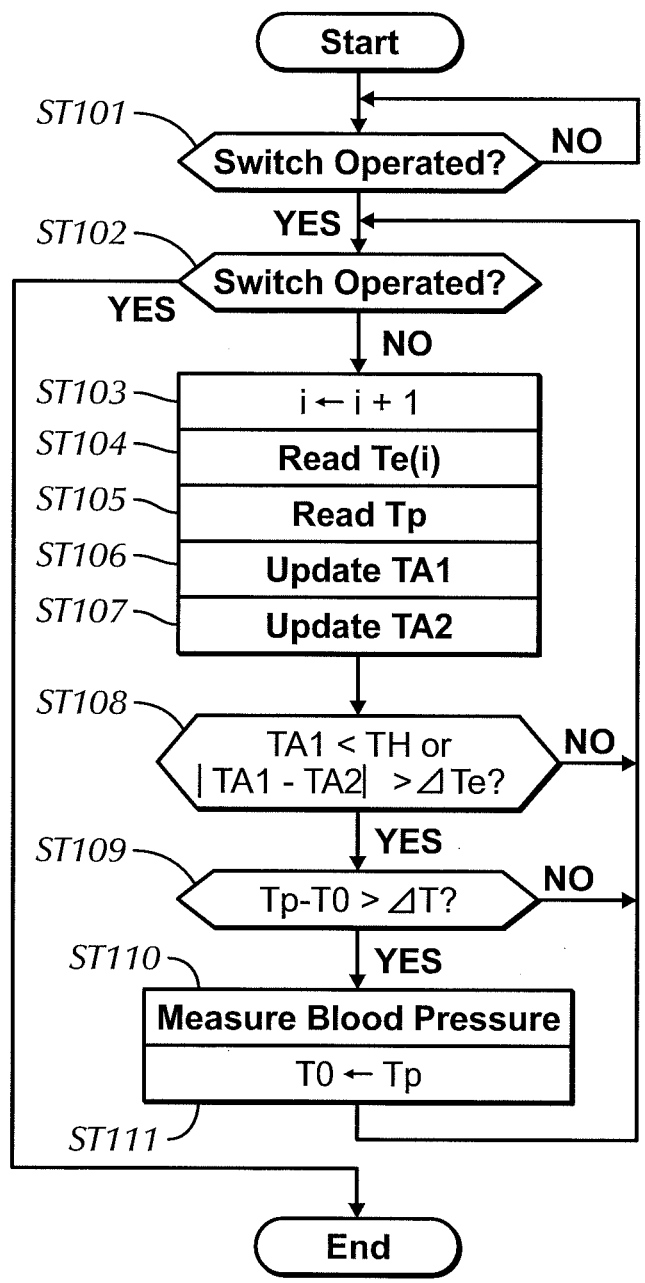
FIG. 17 is a flowchart of measurement processing according to Embodiment 3 of the present invention.

FIG. 17 is a flowchart of measurement processing according to Embodiment 3 of the present invention. A program that conforms to this flowchart is stored in advance in a predetermined storage area of the memory unit 39, and functionality that conforms to this processing flowchart is realized by the CPU 1000B reading out that program from the memory unit 39 and executing it. Note that the later-described variable T0 is a variable set to the time when the most recent blood pressure measurement started, and is set to the initial value of 0 when measurement starts in the flowchart of FIG. 17.

When measurement is to be performed, it is envisioned that the cuff 20 will be fitted at a measurement site on the subject. Before sleeping, the subject powers on the blood pressure measurement apparatus 1B, operates a switch for instructing the start of measurement, and operates a switch for instructing the end of measurement upon getting up.

The CPU 1000B starts performing processing upon receiving the measurement start instruction as a result of the switch operation for starting measurement. The CPU 1000B monitors whether a measurement end instruction has been input as a result of a switch operation during processing as well. If an end instruction is input, processing is forcibly ended even if processing is being executed.

The CPU 1000B then monitors whether an operation for starting measurement was performed using the measurement start switch (step ST101), and when such an operation is performed (YES in step ST101), subsequent processing is started. Next, it is monitored whether or not an operation for ending measurement was performed using the measurement stop switch (step ST102). If the operation for stopping measurement was performed, all operations are ended, and if that operation has not been performed, various variables are initialized, and the procedure moves to the next processing (step ST103).

The trigger output unit 300B increments the variable i, which represents the temperature data time-series, by 1 (step ST103), sets the environmental temperature indicated by the temperature signal from the temperature sensor 48 as a variable Te(i) (step ST104), and sets the current time, which is based on the time data from the timer 43, as the variable Tp (step S105). Here, the interval at which the trigger output unit 300B reads the temperature signal from the temperature sensor 48 is set to 5 sec, for example.

Next, the trigger output unit 300B uses later-described Equation 1 and Equation 2 to update variables TA1 and TA2, which are set as values for evaluating whether a rapid change occurred in the environmental temperature (steps ST106 and ST107).

The following describes the calculation equations used to update the values of the variables TA1 and TA2 in steps ST106 and ST107. In Embodiment 3, operations are realized such that blood pressure measurement is executed after a certain time has elapsed from when a rapid change occurred in the environmental temperature. A certain time period is allowed to elapse in consideration of the time required for a body's blood pressure to react to a rapid change in temperature. The variable TA1 represents the average value of the environmental temperature since a certain time period ago that includes the environmental temperature at that point in time, and the variable TA1 is calculated using Equation 1. The variable TA2 represents the average value of the environmental temperature measured in a time period of the same length as that with the variable TA1, at a time before the variable TA1, and is calculated using Equation 2.

Equation 1

$$TA1 = \sum_{j=i-N}^{i} Te(j)/N \qquad \text{Equation 1}$$

Equation 2

$$TA2 = \sum_{j=i-2N}^{i-N} Te(j)/N \qquad \text{Equation 2}$$

The variable N in Equations 1 and 2 represents the number of pieces of environmental temperature data used in order to calculate the average value, and can be any value. For example, the value of the variable N is 120 in the case where the trigger output unit 300B receives the temperature signal from the temperature sensor 48 every 5 sec (i.e., the environmental temperature data is acquired at a 5-sec interval), and the length of the time period for calculating the average value is 10 minutes.

The trigger output unit 300B determines whether or not the conditional expression (TA1<TH) OR (|TA1−TA2|>ΔTe) holds (step ST108).

This conditional expression represents an expression for determining whether the average value TA1 of the environmental temperature since a certain time period ago that includes the environmental temperature at that time is lower than the pre-set threshold value TH, or whether the absolute value of the difference between the variables TA1 and TA2 is higher than a pre-set threshold value ΔTe. If it is determined that the conditional expression does not hold (NO in step ST108), the processing of steps ST102 to ST108 is repeated.

If it is determined that the conditional expression holds (YES in step ST108), the trigger output unit 300B compares the variable T0 with the variable Tp set to the current time based on the time data received from the timer 43, and determines whether or not the conditional expression Tp−T0>ΔT holds (step ST109). Here, the variable ΔT represents the time period for which the start of blood pressure measurement is prohibited, which is a pre-set time period.

If the trigger output unit 300B determines that the conditional expression does not hold (NO in step ST109), the procedure returns to step ST102, and processing is repeated from there.

On the other hand, if it is determined that the conditional expression holds (YES in step ST109), the trigger output unit 300B outputs the trigger TR to the blood pressure measurement unit 100. Accordingly, blood pressure measurement is started (step ST110). When blood pressure measurement is started, the trigger output unit 300B sets the current time indicated by the variable Tp as the variable T0 (step ST111). Thereafter, the procedure returns to step ST102, and processing is repeated from there until the measurement stop switch is operated.

In Embodiments 1 to 3 described above, ambient environment information and physiological information that is related to the subject's body but excludes the blood pressure were given as examples of information related to blood pressure variation, that is to say, information indicating the factor (event) causing the blood pressure variation. Although blood oxygen saturation level and respiratory pattern were given as examples of physiological information, and ambient temperature was given as an example of ambient environment information, these are merely examples, and other types of information may be applied.

Embodiment 4

A measuring method conforming to any of the flowcharts in the above-described embodiments can be provided as a program. Such a program can be provided in the form of a program product that is recorded on a computer-readable recording medium such as a flexible disk, a CD-ROM, a ROM, a RAM, or a memory card that is supplied to a computer. Alternatively, the program can be provided in the form of being recorded on a recording medium such as a hard disk built into a computer. The program can also be provided by downloading via a network. For example, in the configuration shown in FIG. 1, the blood pressure measurement apparatus 1A that includes the CPU 1000A and has the functionality of a computer can be supplied with the program using any of various types of recording media, such as the SD memory card 47. The CPU 1000A reads out the program stored on the recording medium via the external I/F 45 and executes it.

The program product that is provided is installed in a program storage unit such as a hard disk, and is read out and executed by a CPU. Note that the program product includes the program itself and the recording medium on which the program is recorded.

The embodiments disclosed here are to be considered as examples in all respects and not as limiting in any way. The scope of the present invention is defined by the claims, not the above description, and all changes that come within the meaning and range of equivalency of the claims are intended to be embraced therein. Also, all possible combinations of the embodiments described above are intended to be embraced in the present invention.

REFERENCE SIGNS LIST 1A, 1B Blood pressure measurement apparatus
46 Information processing apparatus
48 Temperature sensor
50 Sensor unit
50B Airflow sensor
100 Blood pressure measurement unit
300A, 300B Trigger output unit
391 Measured data storage portion

The invention claimed is:

1. A blood pressure measurement apparatus for measuring blood pressure in a predetermined period, comprising:
a blood pressure measuring unit that measures the blood pressure of a subject;
an information acquiring unit that acquires information that is related to variation in blood pressure and changes in a time-series in the predetermined period;
a determining unit that determines whether or not the information acquired by the information acquiring unit satisfies a predetermined condition; and
a trigger output unit that, in a case where the determining unit determines that the predetermined condition is satisfied, causes the blood pressure measuring unit to start and execute blood pressure measurement,
wherein the predetermined condition is expressed as a function of time that varies and is measured in the predetermined period,
wherein the predetermined condition includes a threshold value,
wherein the function is a function that changes the threshold value in accordance with the length of elapsed time from when the blood pressure measuring unit was most recently started, and
wherein the determining unit acquires a feature value based on a value indicated by the information in a process of change in the time-series, and calculates the threshold value using the feature value.

2. The blood pressure measurement apparatus according to claim 1, wherein the function is a function that sets an amount of change of the threshold value higher the longer the elapsed time is.

3. The blood pressure measurement apparatus according to claim 1, wherein the information acquired by the information acquiring unit indicates physiological information excluding the blood pressure of the subject.

4. The blood pressure measurement apparatus according to claim 3, wherein the physiological information includes a blood oxygen saturation level of the subject.

5. The blood pressure measurement apparatus according to claim 4, wherein the feature value indicates a local minimum value of the blood oxygen saturation level.

6. The blood pressure measurement apparatus according to claim 4, wherein a rate of change of the threshold value in accordance with the length of the elapsed time is 10% per hour.

7. The blood pressure measurement apparatus according to claim 3, wherein the physiological information includes a respiratory pattern of the subject.

8. The blood pressure measurement apparatus according to claim 7, wherein the feature value indicates the length of an apneic period.

9. The blood pressure measurement apparatus according to claim 1, wherein the information acquired by the information acquiring unit indicates an environmental condition at the time of blood pressure measurement.

10. The blood pressure measurement apparatus according to claim 9, wherein the environmental condition indicates the ambient temperature with respect to the subject at the time of blood pressure measurement.

* * * * *